United States Patent
Wang et al.

(10) Patent No.: US 10,653,772 B2
(45) Date of Patent: May 19, 2020

(54) HEPATITIS B TREATMENT VACCINE ON THE BASIS OF INACTIVATED, WHOLE RECOMBINANT HANSENULA POLYMORPHA CELLS EXPRESSING HBSAG

(71) Applicant: Hemu Wang, Tianjin (CN)

(72) Inventors: Hemu Wang, Tianjin (CN); Changhua Wang, Tianjin (CN); Jun Yang, Tianjin (CN)

(73) Assignee: Hemu Wang, Tianjin (CN)

( * ) Notice: Subject to any disclaimer, the term of this patent is extended or adjusted under 35 U.S.C. 154(b) by 0 days.

(21) Appl. No.: 16/088,169

(22) PCT Filed: Mar. 16, 2017

(86) PCT No.: PCT/CN2017/076933
§ 371 (c)(1),
(2) Date: Feb. 15, 2019

(87) PCT Pub. No.: WO2017/162091
PCT Pub. Date: Sep. 28, 2017

(65) Prior Publication Data
US 2019/0216921 A1    Jul. 18, 2019

(30) Foreign Application Priority Data
Mar. 25, 2016    (CN) .......................... 2016 1 0180329

(51) Int. Cl.
| | | |
|---|---|---|
| *A61K 39/00* | (2006.01) | |
| *C07K 14/02* | (2006.01) | |
| *A61K 47/46* | (2006.01) | |
| *C07K 14/005* | (2006.01) | |
| *A61K 36/06* | (2006.01) | |
| *A61K 39/29* | (2006.01) | |
| *A61K 39/39* | (2006.01) | |
| *A61P 31/20* | (2006.01) | |
| *C12N 7/00* | (2006.01) | |
| *C12R 1/78* | (2006.01) | |

(52) U.S. Cl.
CPC ............ *A61K 39/292* (2013.01); *A61K 39/29* (2013.01); *A61K 39/39* (2013.01); *A61P 31/20* (2018.01); *C07K 14/005* (2013.01); *C07K 14/02* (2013.01); *C12N 7/00* (2013.01); *A61K 2039/521* (2013.01); *A61K 2039/523* (2013.01); *A61K 2039/5258* (2013.01); *A61K 2039/55588* (2013.01); *C12N 2730/10122* (2013.01); *C12N 2730/10134* (2013.01); *C12R 1/78* (2013.01)

(58) Field of Classification Search
CPC .. C07K 14/005; C12N 7/00; A61K 2039/523; A61K 39/12; A61K 2039/5158
See application file for complete search history.

(56) References Cited

FOREIGN PATENT DOCUMENTS

CN          102038948          *  5/2011

* cited by examiner

*Primary Examiner* — Barry A Chestnut
(74) *Attorney, Agent, or Firm* — Li & Cai Intellectual Property (USA) Office

(57) ABSTRACT

A hepatitis B treatment vaccine on the basis of inactivated, whole recombinant *Hansenula polymorpha* cells expressing HBsAg. The vaccine is the HBsAg expressed in recombinant *Hansenula polymorpha* cells. $10^8$ cells contain 6-10 μg HBsAg as an antigen; the vaccine contains a total of 16-21 HBsAg-specific CTL epitopes; the vaccine uses optimized inactivated, fully recombinant *Hansenula polymorpha* cells as an adjuvant.

10 Claims, 5 Drawing Sheets
Specification includes a Sequence Listing.

HEPATITIS B TREATMENT VACCINE ON THE BASIS OF INACTIVATED, WHOLE RECOMBINANT HANSENULA POLYMORPHA CELLS EXPRESSING HBSAG

FIELD OF THE DISCLOSURE

The present disclosure relates to a field of genetic engineering, and more particularly to a hepatitis B vaccine including hepatitis B surface antigen adw2 (HBsAg-adw2) expressed by recombinant *Hansenula polymorpha* cells.

BACKGROUND OF THE DISCLOSURE

HBV (hepatitis B virus, HBV) infection is a serious public health problem. According to the World Health Organization (WHO), about 20 million people have been infected with HBV within 6 billion people worldwide, of which 350 million people have chronic HBV infection; about 1 million people die each year from liver failure, cirrhosis and primary hepatocellular carcinoma (liver cancer) caused by HBV infection. Liver cancer patients worldwide, more than 75% is caused by HBV. China is an endemic area of HBV infection. The Ministry of Health of China incorporated hepatitis B vaccine into planned immunization management in 1992. According to the national hepatitis B serological surveys in 2006, after nearly 15 years of efforts, the general population in China, especially children under the age of 15, HBV infection rate has significantly decreased. Due to history background, about 93 million people are suffering from chronic HBV infection in China, including about 20 million patients with chronic hepatitis B. It is estimated that liver cirrhosis and liver cancer due to HBV cause nearly 300,000 death cases each year, wherein new hepatitis B are about 0.5 to 1 million cases. HBV disease is still an important factor that endangers people's health, hinders social development, and affects social stability for a long time. It is a serious public health problem in people-oriented society, and also a priority major health issue in China. According to the survey, the annual direct and indirect medical expense for chronic hepatitis B (including liver cirrhosis and liver cancer) in China is about 680 billion. How to effectively treat existing hepatitis B virus infection patients and hepatitis B patients has become a major problem that needs to be resolved first in the prevention and treatment of hepatitis B.

Hepatitis B vaccine immunization prevention is the most effective way to reduce the burden of disease. Gene recombination technology is the core technology of modern biotechnology; also is the mainly technology of the large-scale production of hepatitis B vaccine, and the only technology of virus-like particle hepatitis B virus surface antigen (HBsAg VLP). Saccharomyces cerevisiae was the first eukaryotic system to express foreign genes. However, there are still many shortcomings in the industrial production of *S. cerevisiae* expression system. For example, the exogenous gene plasmids of engineering strain are free in the cytoplasm lead to genetically unstable; the fermentation density is not enough to low production efficiency; the synthesized polypeptide chain is often hyperglycosylated. The applicant has been involved in the research and development of *Hansenula polymorpha* (*H. polymorpha*) recombinant hepatitis B vaccine since 1995. In 1998 to 2002, in Dalian Gaoxin Bio-Pharmaceutical Co., Ltd., the *H. polymorpha* recombinant HBsAg-adr2 hepatitis B vaccine was developed. The yield of HBsAg VLP pure stock solution was 40 mg/L, and it has been approved since 2002 in China. In 2003 to 2006, the applicant assisted Beijing Tiantan Biological Products Co., Ltd. to develop recombinant *H. polymorpha* HBsAg-adr2 hepatitis B vaccine. The pure stock solution of HBsAg VLP has a yield of 85 mg/liter or more; it has been submitted to the National New Drug Review in 2015, and the China patent publication number based on the vaccine is CN104232661A.

The pathogenesis of hepatitis B identified according to the prior art is as follows: After HBV infection, the HBV carriers can be generally divided into immune tolerance phase, immune clearance phase, and residual or inactive phase. The immune tolerance phase is characterized by high levels of HBV replication, positive serum HBsAg and HBeAg, high HBV DNA level ($>10^5$ copies/ml), normal alanine aminotransferase level (ALT), and no obvious abnormalities in liver histology. The immune clearance phase is characterized by serum HBV DNA level $>10^5$ copies/ml, but generally lower than the immune tolerance phase, normal or intermittently elevated aspartate aminotransferase (AST) level, and necrotic inflammation shown in liver histology. The residual or inactive phase is characterized by HBeAg-negative, anti-HBe-positive, could not be detected (PCR assay) or below the lower limit of detection, level normal, and no obvious inflammation in liver histology. However, HBV infection in adolescents and adults generally does not start from the immune tolerance phase, but initial from the immune clearance phase, which is manifested as acute hepatitis B, of which only 5%-10% develop chronic hepatitis B. However, the exact pathogenesis is still unknown.

Anti-hepatitis B virus treatment is currently the main treatment for hepatitis B virus infection and hepatitis B patients. At present, anti-hepatitis B virus drugs mainly include interferon-based immunomodulators and nucleotide analogues against HBV DNA polymerase. Although they have certain curative effects, they are not satisfactory, and most patients cannot be cured. Interferon can induce HBsAg seroclearance or seroconversion in few patients, but its high cost, need to be injected, and has certain side effects. Nucleotide analogs act on HBV DNA polymerase, which only inhibits viral replication, does not completely eliminate HBV DNA and cccDNA, and easily lead to viral resistance mutation by long-term therapy.

Therefore, in order to completely eliminate HBV and cccDNA, to develop a new and more effectively of HBV hepatitis B vaccine is urgent need. The low immune rejection of liver transplantation indicates that the human liver is an immune-tolerant organ. Liver is the target organ of hepatitis B virus (HBV) infection, so that the immune tolerance to HBV in liver is a major feature. Reversal of HBV immune tolerance is the base for the development of immunotherapy vaccine for chronic hepatitis B (CHB) patients. HBV immune tolerance is not only reflected anti-HBV immune response failed to effectively eliminate the virus in local liver, leading to persistent infection, but also reflected in the persistence of HBV, leading the systemic immune system with no response to the HBV, such as the patient in HBV immune tolerance phase is no response to HBsAg vaccine. This is also the main reason why current therapeutic vaccines are difficult to succeed in CHB patients. Liver-induced immune tolerance and its reversal mechanism will provide a theoretical basis for the development of hepatitis B vaccine.

Recent data suggest that initial CD8+T (CTL) cell activation occurs in the liver, while pre-inflammatory (i.e. innate immune activation) increases the number of survival CTLs, makes CTLs more effectively, resulting in a liver immune response to eliminate the infected HBV. In the absence of inflammation in advance (ie, innate immunity is not activated, such as infants and young children), the function of CTL is impaired and the half-life of CTL is short, resulting in liver tolerance to HBV. However, initial HBV antigen encounter immunity induced high-efficiently activated HBV CTLs in the lymph nodes outside the liver, and then into the liver, which also increases the number of survival CTLs, makes CTLs more effectively, resulting in a liver immune response to eliminate the infected HBV. This immune mechanism for the two sites provides a theoretical basis for the development of subcutaneous and intramuscular injection of hepatitis B vaccine, which leads to liver immune response and HBV clearance.

According to the journal "A Whole Recombinant Yeast-Based Therapeutic Vaccine that is comprised of heat-inactivated, whole recombinant Saccharomyces cerevisiae yeast cells expressing disease-related antigens" of Thomas H. King (US) in 2014, which relates to a therapeutic vaccine based on a heat-inactivated, whole recombinant Saccharomyces cerevisiae yeast cells expressing disease-related antigen. The study pioneered a therapeutic vaccine platform that uses intracellular recombinantly expressed proteins as antigens and heat-inactivated whole Saccharomyces cerevisiae cells as adjuvant. In addition, the HBV antigen expressed by a hepatitis B therapeutic vaccine (which has been numbered as GS4774 under the platform) is an x-s-core antigen as fusion protein. This yeast vector provides multiple antigens into the MHC class I and class II antigen presentation pathways, stimulates potent CD4+ and CD8+ cell responses, and disrupts antigen tolerance in immunogenic mouse model. The yeast vector is also not easily being neutralized in body, and is therefore suitable for repeated administration to obtain long-term immunological stress, ideally eliminating chronic intracellular infections such as HCV and HBV.

According to the journal of Huang in 2010, β-Glucan particles (GPs) which are purified from Saccharomyces cerevisiae cell walls have >85% β1,3-d-glucan polymers, ~2% chitin, and <1% lipids and protein, with the rest being mostly ash and moisture. In in vitro T-cell proliferation assays, ovalbumin (OVA) was complexed into the hollow GP shells (GP-OVA) to as vaccine, and free OVA as control antigen. At concentrations from 0.03 μg/ml to 0.5 μg/ml, GP-OVA stimulated OT-I and OT-II T-cell proliferation. In contrast, free OVA failed to stimulate proliferation of either OT-I or OT-II T cells. In order to achieve similar stimulation effects of GP-OVA, 100 times or higher concentrations of free OVA were required. These results demonstrate that: (1) Virus-like particle GPS is an efficiently t agonist of the Dectin-1 receptor. (2) Compared with free OVA, antigens delivered in Virus-like particle GP-OVA were more efficiently processed and presented by DCs (dendritic cells).

In 2003 to 2005, American scientists reported the results of a series of studies on hepatitis B virus infection in chimpanzees. The mechanism controlling disease is the covalently closed circular DNA (cccDNA) of the hepatocyte nuclear HBV pool. The HBV-specific CD8+T (CTL cells), which produce INF-γ, massively influx into liver and target to hepatocytes infected with HBV, and the cccDNA clearance and hepatocytes infected HBV reversion are related to the INF-γ produced by liver CD8+ T cells. These results suggest that cccDNA clearance is a two-step process mediated by cellular immune responses: In the first step is to reduce the pool of cccDNA molecules by more than 90% without cell damage, thereby eliminating the precursor of HBV-relaxed circular deoxyribonucleic acid, and the second step is to improve the process of destroying infected liver cells and trigger an immune reversion.

In 2014, Dr. Zeng Zhutian of the University of Science and Technology of China reported that, by hydrodynamic injection of HBV persistent mouse mimic the immune tolerance phase of chronically infected HBV patients, the combination therapy of IL-12 pretreatment with IL-12 and HBsAg VLP vaccine, which is called IL-12-based vaccine therapy, can effectively reverse HBV systemic immune tolerance, and lead to HBV clearance. The levels of follicular-like helper T cells (Tfh, which are in lymph node) and germinal center B cells (GC B) of HBV mice were significantly increased after undergoing IL-12-based vaccine therapy. Correspondingly, HBsAg-specific IgG-producing cells in spleen cells were also significantly increased, and most of the mice showed protective antibody anti-HBs in the serum of the late treatment. In addition, the ability of T cells to stimulate HBsAg stimulation in vitro was also significantly restored after IL-12 combination vaccine treatment.

The China patent publication number CN102038948A described that hepatitis B vaccine immunized healthy mice with whole recombinant *H. polymorpha* cells expressing HBsAg VLP antigen, and achieved well results at the cellular and protein molecular levels: induction of the activation, maturation and proliferation of high-level dendritic cells (DCs), induction of extremely high-level of anti-HBs immune response, Induction of higher level of IFN-γ secretion, and result in a significant HBsAg-specific CTL (cytotoxic T lymphocyte) response. It guides the development of chronic hepatitis B vaccine. The test mice were immunized with high doses: $2 \times 10^8$ recombinant *H. polymorpha* cells and 2 μg hepatitis B surface antigens (about 20 times the half effective dose of the ED50 test in mice) it expressed was the key that obtained good results. However, there is a safety limit for the number of recombinant *H. polymorpha* cells used for human injection ($8-12 \times 10^8$ recombinant *H. polymorpha* cells). The expression level of HBsAg VLP antigen in recombinant *H. polymorpha* cells disclosed in is too low, when intended for human injection which a single injection of low dose of HBsAg, is difficult to exert a therapeutic effect of this vaccine. Moreover, CN102038948A does not mention any HBsAg-specific CTL epitopes and heat-inactivation processes. Therefore, providing recombinant *H. polymorpha* cells having a high expression level of HBsAg VLP antigen and preferably a HBsAg-specific CTL epitope and a heat inactivation process, so as to provide a hepatitis B therapeutic vaccine based on inactivated whole recombinant *H. polymorpha* cell expressing HBsAg has become an important issue in the art.

SUMMARY OF THE DISCLOSURE

In response to the above-referenced technical inadequacies, the present disclosure provides a hepatitis B therapeutic vaccine based on inactivated whole recombinant *H. polymorpha* cells expressing HBsAg. The hepatitis B therapeutic vaccine uses the recombinant *H. polymorpha* cells as an adjuvant, 6-10 μg of the HBsAg per $10^8$ the recombinant *H. polymorpha* cells as antigen; and each HBsAg has 16-21 HBsAg-specific CTL epitopes.

In certain embodiments, the HBsAg expressed by there combinant *H. polymorpha* cells includes 19 CTL epitopes as follow: VLQAGFFLL, PFVQWFVGL, FLLTRILTI, WYWGPSLYSI, SLNFLGGSPV, FLGGSPVCL, LYSIVSPF, LYSIVSPFI, PFIPLLPIF, LLLCLIFLL, LLCLIFLLV, LLDYQGMLPV, LVLLDYQGML, VLLDY- QGML, WLSLLVPFV, LLVPFVQWFV, GLSPTVWLSA, SIVSPFIPLL, and LLPIFFCLWV.

In certain embodiments, the HBsAg is adw subtype, and the DNA sequence of the recombinant *H. polymorpha* cell is shown as SEQ ID NO: 1. In certain embodiments, the amino acid sequence of the HBsAg is shown as SEQ ID NO: 2.

In certain embodiments, the HBsAg expressed by there combinant *H. polymorpha* is a virus-like particle structure, which is formed by inserting HBsAgs into *H. polymorpha* lipid, and 9 to 12 among the 14 cysteic acids of the HBsAg form disulfide bonds.

In certain embodiments, the conditions of inactivation of the inactivated whole recombinant *H. polymorpha* are: inactivation temperature from 52° C. to 54° C., and inactivation time from 1 hour to 3 hours.

In certain embodiments, the host *H. polymorpha* cell line of the recombinant *H. polymorpha* is HU-11, and the accession number is CGMCC No. 1218, and the disrupted DNA sequence of the orphanin-5-phosphate decarboxylase gene of the host *H. polymorpha* is shown in SEQ ID NO: 3.

In certain embodiments, the hepatitis B therapeutic vaccine further includes HBsAg stock solution or aluminum adjuvant HBsAg.

In certain embodiments, the dosage form of the hepatitis B therapeutic vaccine is selected from pre-filled injection solution, injection solution, and lyophilized powder injection.

In one aspect, the present disclosure provides a recombinant *H. polymorpha*, which includes the nucleotide sequence of SEQ ID NO: 1, and the nucleotide sequence of SEQ ID NO: 1 is integrated into the genome of the recombinant *H. polymorpha*.

In certain embodiments, the host *H. polymorpha* cell line of the recombinant *H. polymorpha* is HU-11, and the accession number is CGMCC No. 1218, and the disrupted DNA sequence of the orphanin-5-phosphate decarboxylase gene of the host *H. polymorpha* is shown in SEQ ID NO: 3.

The present disclosure provides a hepatitis B therapeutic vaccine based on recombinant *H. polymorpha* cells expressing HBsAg, which is based on a recombinant *H. polymorpha* cells having a novel high-level HBsAg expression. Since the recombinant *H. polymorpha* contains 6-10 µg of HBsAg per $10^8$ cells, the injection amount of HBsAg can be maximized and the amount of HBsAg injected can be maximized within the upper limit of the human injection of the existing recombinant *H. polymorpha* cells as an adjuvant, so as to enhance the reversal of immune tolerance status in patients with hepatitis B. The inactivated whole recombinant *H. polymorpha* cells is the efficiently agonist of the Dectin-1 receptor of dendritic cells (DC, which are the most efficient antigen-presenting cells). In addition, the HBsAg expressed by recombinant *H. polymorpha* cells of the present disclosure has 19 specific CTL epitopes, and CTLs cells target HBV-infected hepatocytes and release IFN-γ: In the first step is to reduce the pool of cccDNA molecules more than 90% without hepatocyte damage, and the second step is to improve the process of destroying infected hepatocytes and trigger HBV immune reversion. In certain embodiments, the immunogenicity and reactivity of the preferred HBsAg are further improved by expressing the DNA sequence (SEQ ID NO: 1) of preferably HBsAg, preferably 19 CTL epitopes in 21 CTLs. Moreover, the present disclosure is also preferred the optimized inactivation process of the recombinant *H. polymorpha* cells, thereby ensuring the efficiency and safety of the vaccine.

BRIEF DESCRIPTION OF THE DRAWINGS

FIG. 1 is a schematic view showing the construction process of plasmid pMPT-HBs adw2;

FIG. 5 is a flow chart showing the steps of transformation and screening of recombinant *H. polymorpha* in the second embodiment.

DETAILED DESCRIPTION OF THE EXEMPLARY EMBODIMENTS

Figure 2:
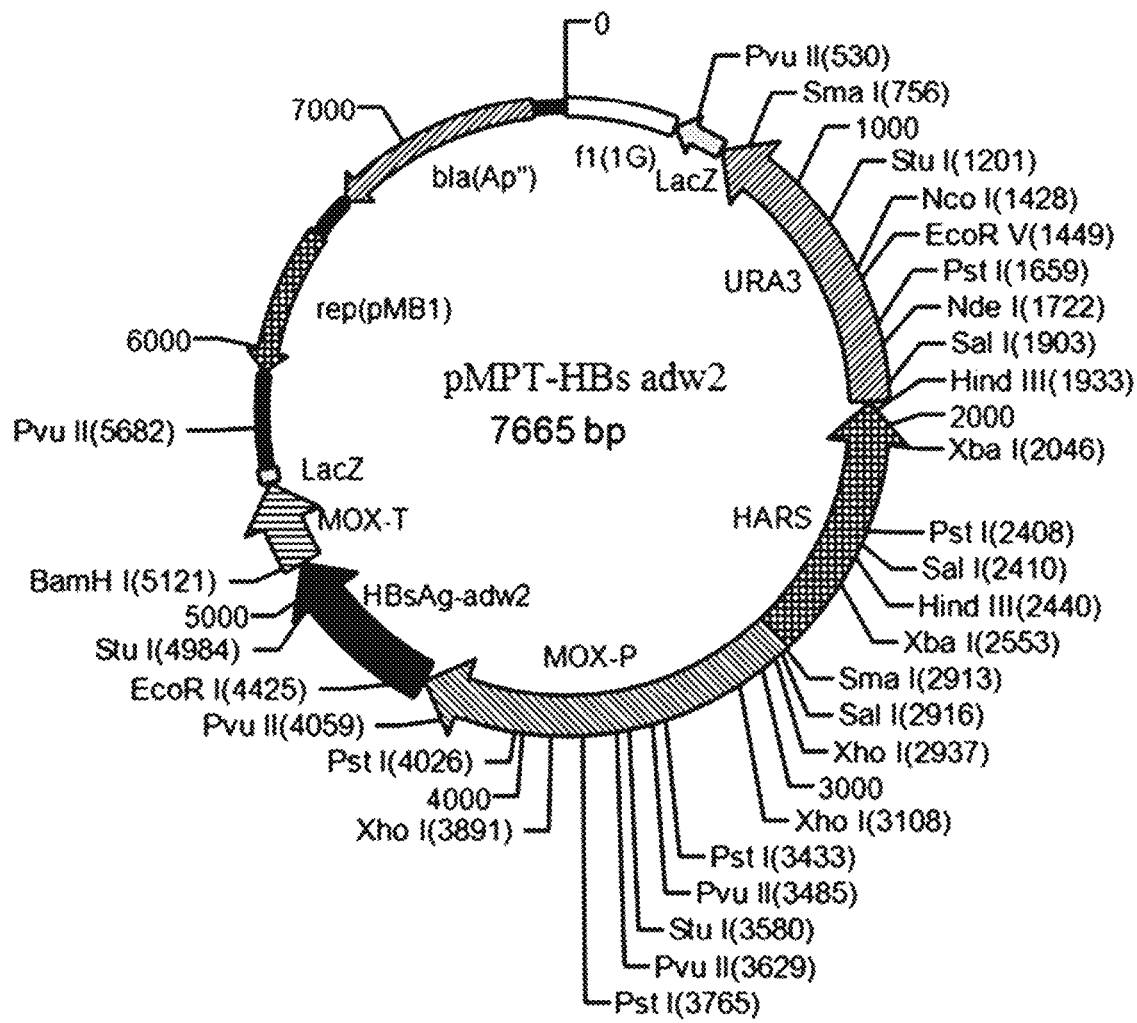
FIG. 2 is a physical map of plasmid pMPT-HBs adw2.

The construction of the *H. polymorpha* intracellular plasmid pMPT-02, which is the applicant's non-exclusive proprietary technology:

1.5 kb *H. polymorpha* MOX (methanol oxidase) promoter, 350 bp *H. polymorpha* MOX (methanol oxidase) terminator, 1.0 kb *H. polymorpha* autonomous replication sequence HARS, and 1.1 kb Saccharomyces cerevisiae uracil gene ScURA3 were tightly ligated by gene synthesis technology element, and then inserted into the pBluescripII plasmid to construct a shuttle plasmid pMPT-02.

Development of the Host Cell Using the Uracil Auxotrophic URA3-Host Cell Line HU-11:

A recombinant *H. polymorpha* (*H. polymorpha*) strain HU-11 (CGMCC No. 1218) in which the orotidine-5-phosphate decarboxylase gene (HURA3) was disrupted by homologous sequence-mediated homologous integration. Compared with the conventional auxotrophic host strains produced by mutagenesis, the recombinant *H. polymorpha* strain HU-11 has the characteristics of high genetic stability and low back mutation rate. It was convenient for genetic transformation and screening of recombinant strains, and maintains the wild-type strain. The physiological and biochemical characteristics were beneficial to the culture of recombinant strains and the high expression of foreign proteins, and have high industrial application value. The DNA sequencing result of the disrupted URA3 gene of the *H. polymorpha* host strain HU11 showed that the five bases of GAAGT were inserted into the 31st base. The insertion of five bases of GAAGT produces a frameshift mutation. The frameshift mutation resulted in a mutation in all of the 254 amino acid codes after the 11th position, and the mutation produced a total of 15 termination codes, indicating that the structural gene of URA3 is no longer re-expressible. The probability that the five bases GAAGT simultaneously produce a back reversion mutation was extremely small. The experimental test also proved that the back mutation rate of the host strain HU11 is zero. This low back-reversion mutation rate of the host strain was particularly advantageous for transformation screening. URA3-ogal deficiency host cell line HU-11 (CGMCC No. 1218) established by gene knock out technology was disclosed in the applicant's previously invention CN1651570A. The DNA sequence in which the disrupted decarboxylase gene (HURA3) is shown in SEQ ID NO: 3.

The DNA sequence of HBsAg expression of the recombinant *H. polymorpha* of the present disclosure is based on the HBsAg adw2 subtypes as shown in SEQ ID NO: 1. The amino acid sequence of the HBsAg is shown in SEQ ID NO: 2.

Construction of the *H. polymorpha* Intracellular Plasmids pMPT-HBs adw2:

A synthetic nucleotide sequence according to the sequence of SEQ ID NO: 1 (hereinafter referred to as HBsAg adw2 gene) was constructed into a glycerol strain containing the HBsAg adw2 gene plasmid; the plasmid after correct sequencing was digested with EcoRI/BamHI, and then 701 bp DNA fragment was obtained.

The correct plasmid pMPT-02 was digested with EcoRI/BamHI, and the vector DNA obtained after the gelatinization was ligated to obtain the *H. polymorpha* intracellular plasmid pMPT-HBs adw2, and the plasmid pMPT-HBs adw2 was transformed into *E. coli* Competent Cell JM109 (Code No. D9052), and then was cultured overnight by plating on. Single colonies were selected from the transformation plates, plasmid DNA was extracted and digested with EcoRI/BamHI, and the results of restriction enzyme digestion showed positive clones. Sequencing confirmed that the plasmid pMPT-HBs adw2 was correct.

Figure 1:
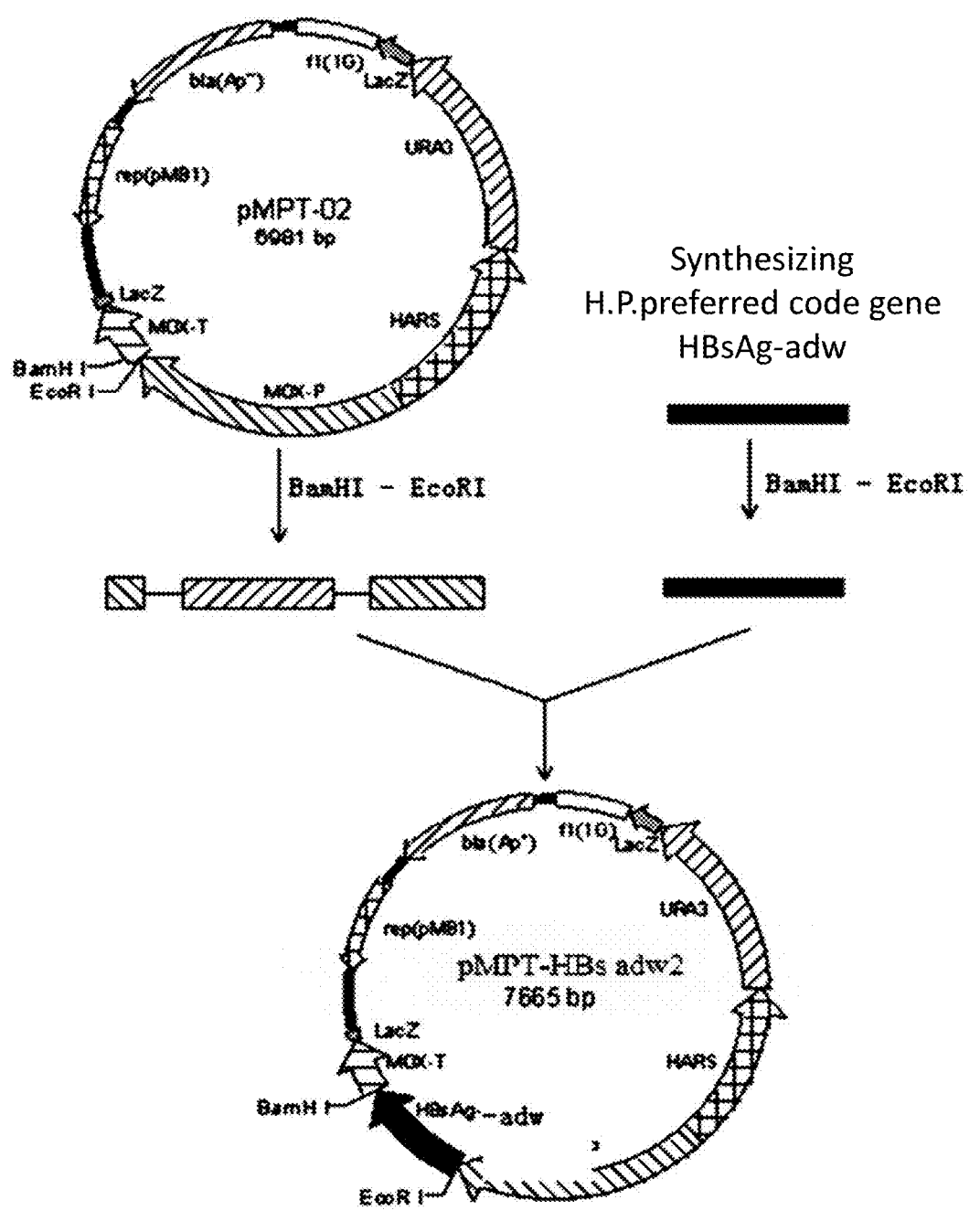

The HBsAg adw2 gene was inserted into the multiple cloning site of the *H. polymorpha* expression system intracellular plasmid pMPT-02: between EcoRI and BamHI. The full length of the plasmid pMPT-HBs adw2 was 7665 bp. A schematic diagram of the construction process of plasmid pMPT-HBs-adw2 was shown in FIG. 1. The physical map of the pMPT-HBs adw2 plasmid was shown in FIG. 2.

Construction of Recombinant *H. polymorpha* Hepatitis B Virus Surface Antigen (HBsAg) adw2 Subtype Engineering Strain:

In order to construct the recombinant *H. polymorpha* hepatitis B virus surface antigen (HBsAg) adw2 subtype engineering strain, the cell electroporation technology developed by the applicant was applied. The RC pulse: amplitude 1500V, capacitance 22 μf, and time constant 3-5 ms electric shock 1 time, adopted the pMPT-HBsadw2 plasmid transformed into *H. polymorpha* cells of the HU-11 strain (CGMCC No. 1218) from which the URA3-gene was knocked out. The single colony transformants were picked up on the MD selection culture plate and transferred to the MD liquid medium for continuous subculture. The adw2 subtype HBsAg gene and the corresponding regulatory components were multi-copy and heterologously integrated into the host *H. polymorpha* cell chromosome. After a single colony of more than one thousand transformant single colonies, the following three steps were screened:

(1) Clonal strains with large single colonies and fast cell growth have a high probability of multiple copies.

(2) The PCR technique was used to compare the electrophoretic band luminance of the HBsAg gene and the single copy number MOX (methanol oxidase) gene, and the HBsAg gene copy number was determined semi-quantitatively.

(3) The expression level of HBsAg released after methanol-induced and shake flask culture for 72 hours was detected.

The application of PCR technology to transformants screening was a new creation of this application. The multiple copies of the foreign gene HBsAg are determined and heterologously integrated in the *H. polymorpha* chromosome, while the MOX gene in the *H. polymorpha* chromosome was intact and not destroyed. They all play an important role and show unique advantages of the *H. polymorpha* expression system. A pair of primers were designed to simultaneously amplify the MOX gene (single copy) and the heterologous integrated HBsAg foreign gene (multi-copy) in the *H. polymorpha* chromosome. By comparing the brightness of the bands of the amplified product in agarose gel electrophoresis, it was possible to roughly determine whether the HBsAg gene was multiple copies. This method was used for the preliminary screening of multi-copy strains of engineered HBsAg gene. The amplified HBsAg fragment was 800 bp in length and the amplified MOX fragment was 2000 bp in length.

Design using primer sequences:

```
primer forward:   5'-TCAAAAGCGGTATGTCCTTCCACGT-'3
primer reverse:   5'-TACTGCTGCCAGTGCACGGTG-'3
```

Figure 3:
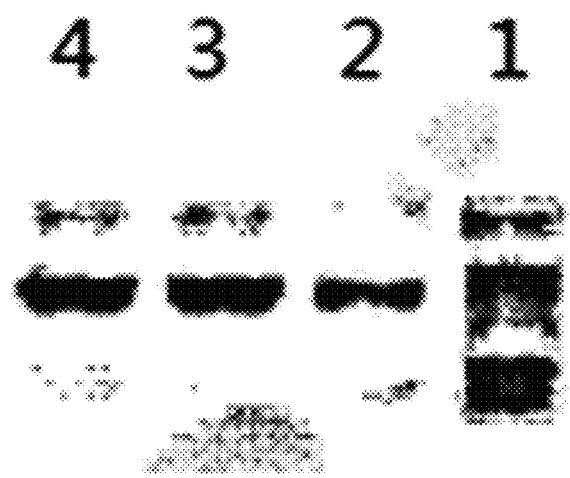
FIG. 3 is an electrophoresis photograph of a PCR amplification product of the engineered strain obtained by screening.

PCR product agarose gel electrophoresis: the amplified product of HBsAg gene of engineering strain was about 800 bp, and the amplification product of *H. polymorpha* single copy gene MOX gene was about 2000 bp. The electrophoresis photograph of the PCR amplification product of the engineered strain obtained by screening was shown in FIG. 3, wherein 1 was Marker. The recombinant *H. polymorpha* hepatitis B virus surface antigen (HBsAg) engineering strain obtained by final screening is numbered as HS604-5.

Determination of Intracellular HBsAg VLP Expression in Recombinant *H. polymorpha* Fermentation Broth:

10 μg of adr2 subtype HBsAg hepatitis B surface antigen lyophilized standard provided by Tiantan Biotechnology was diluted with diluent to dilute to 1024 ng/mL, 512 ng/mL, 256 ng/mL, 128 ng/mL, 64 ng/mL, 32 ng/mL, 16 ng./mL, 8 ng/mL, 4 ng/mL, 2 ng/mL, 0 ng/mL (diluent) a total of 11 standard points, and using radioimmunoassay kit to detect HBsAg reaction.

The obtained engineering strain (No. HS604-5) was subjected to 30 liters of pilot fermentation (batch number 20150422), and 1 mL 10 $OD_{600}$ nm was sampled after 87 hours of fermentation. After disrupting the cells with glass beads (cell disruption rate: 65%), the 200-fold diluted sample and the standard were separately reacted in the radioimmunoassay kit at the same time, and the expression of HBsAg antigen obtained by the γ-counter auto-completed curve was 126.9 (ng/mL). Based on the above, the expression level of intracellular HBsAg antigen in recombinant *H. polymorpha* was calculated as:

$$126.96 \text{ (ng/mL)} \times 200 \div 10 \times 5.0 \times 10^7 \times 65\%/\text{mL} = 7.84 \text{ μg}/10^8 \text{ cells}$$

Figure 4:
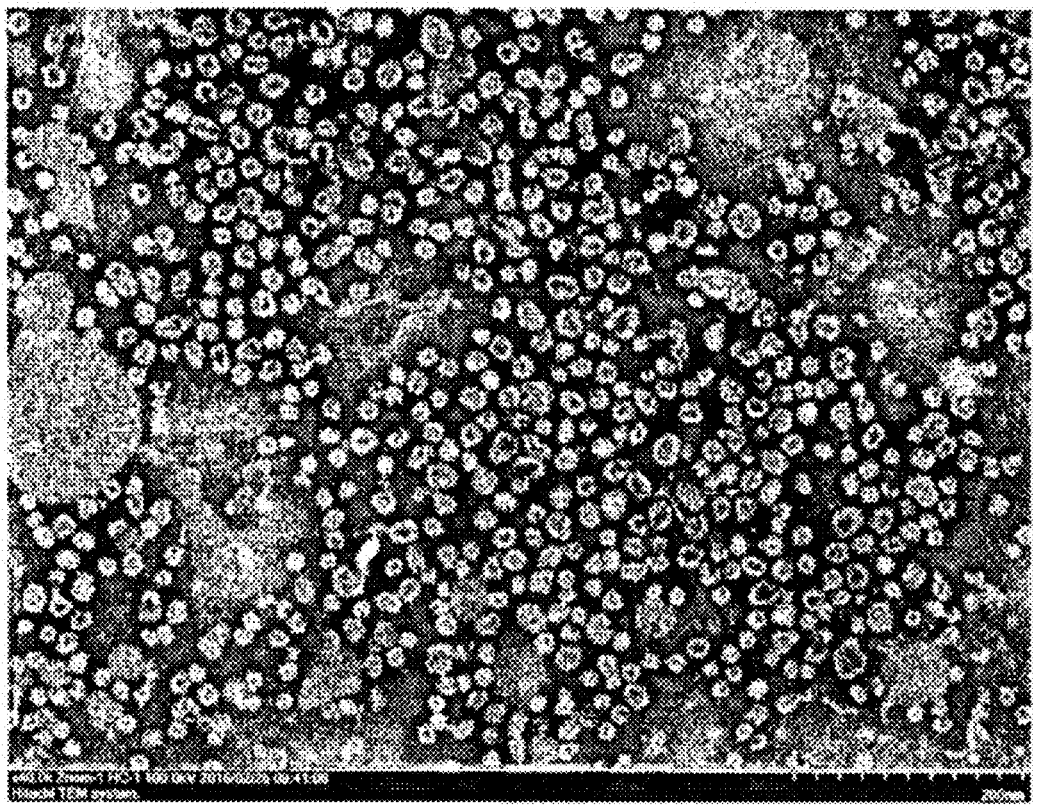
FIG. 4 is an electron micrograph of the pure stock solution of recombinant *H. polymorpha* recombinant HBsAg.

An electron micrograph of the recombinant HBsAg pure stock solution of recombinant *H. polymorpha* was shown in FIG. 4. The results showed that the high purity, high concentration and virus-like particle (VLP) structure of recombinant HBsAg were stable.

Optimization of Heat-Inactivated Recombinant *H. polymorpha* Cell HBsAg Cell Conditions:

In order to determine the optimal conditions for the inactivated recombinant *H. polymorphaa*, the following requirements should be met: (1) Reduce the survival rate of the inactivated recombinant *H. polymorpha* less than 5%. (2) Maintain a complete cellular structure to avoid leakage of heat-inactivated recombinant *H. polymorpha* intracellular antigenic substance. (3) Maintain the thermal stability of HBsAg virus-like particles (VLP) expressed in recombinant *H. polymorpha* cells, so as to avoid the antigenicity decline. The above three requirements are the main condition of the production for the heat-inactivated recombinant *H. polymorpha* expressing HBsAg, and would provide the basis for the development of vaccine manufacturing and verification procedures. In addition, the thermal stability of HBsAg virus-like particle (VLP) expressed in recombinant *H. polymorpha* cells is the first issue to be solved. For this purpose, 16 sets of different temperature (50° C., 52° C., 54° C., 56° C. and 58° C.), and different time (1 hr, 2 hr, and 3 hr) of the heat-inactivation test of recombinant HBsAg *H. polymorpha* cells were designed and set at 20° C. as the control group. During the detection: as the heat inactivation temperature and time increase, the solubility of the outer layer of the cell wall increases, the cell breakage rate increases, and the intracellular HBsAg VLP antigen reactivity peak multiplied at 52° C., 1 hr. The extracellular HBsAg antigen reactivity was extremely low during the temperature and time changes of the heat-inactivation assay, indicating that intracellular HBsAg VLP did not leak out, maintaining the heat-inactivated recombinant *H. polymorpha* cell structure. The survival rate of heat-inactivated cells was as low as 1/50,000 at 56° C., 3 hr. Therefore, a basis for optimizing the conditions for heat inactivation of recombinant *H. polymorpha* cells was provided. Considering various factors, the heat-inactivation process conditions are finally determined as follows: the heat-inactivation temperature is from 52° C.-54° C., and the heat-inactivation time is from 1 hour to 3 hours.

More than 90% of HBsAg-Specific CTL Cells Trigger Reversal of Iimmunity Without Cell Damage The results of a series of studies on hepatitis B virus infection in chimpanzees indicated that, the HBV-specific CD8+ T cells, which produce INF-γ and target to hepatocytes infected with HBV; in the first step is to reduce the pool of cccDNA molecules by more than 90% without cell damage, and the second step is to improve the process of destroying infected liver cells and trigger reversal of immunity.

Based on three experiments described CTL epitopes review, prediction and patented invention reported, HBV capsid antigen (Pre-S1-Pre-S2-HBsAg) has 23 CTL epitopes that did not repeat. The amino acid sequence of the HBsAg antigen of the present disclosure includes the following 19 CTL epitopes: VLQAGFFLL, PFVQWFVGL, FLLTRILTI, WYWGPSLYSI, SLNFLGGSPV, FLGGSPVCL, LYSIVSPF, LYSIVSPFI, PFIPLLPIF, LLLCLIFLL, LLCLIFLLV, LLDYQGMLPV, LVLLDYQGML, VLLDYQGML, WLSLLVPFV, LLVPFVQWFV, GLSPTVWLSA, SIVSPFIPLL, and LLPIFFCLWV.

*H. polymorpha* Recombinant Hepatitis B Vaccine Product is Preferred as Prefilled Injection:

The routinely dispensed recombinant hepatitis B vaccine (yeast) pre-filled syringe was processed thermal stability test at 37° C. for 45 days, and has proved that the relative in vitro relative efficacy (RP) of the vaccine met the requirements, while at the same storage condition, RP of routinely dispensed hepatitis B vaccine did not meet the requirements. Pre-filled syringe-packed recombinant hepatitis B vaccine (yeast) can be transported without refrigerated in a short time, stored and used.

The pre-filled syringe has 1 needle and 1 box, which is easy to use, easy to learn to use and essentials, a disposable syringe cannot be reused. Vaccination without a separate syringe can prevent from infection or infectious diseases spread caused by not completely sterilized glass syringe, the adverse effects caused by improper needle selection or the risk of disposable syringe being reused.

Full vaccination of pre-filled hepatitis B vaccine syringe has a good comprehensive cost-benefit ratio.

The following embodiments are intended to be illustrative, and not restrictive, and the scope of the present disclosure is not limited by the following embodiments.

First Embodiment

The pMPT-HBsAg adw2 plasmid was constructed based on the sequence of SEQ ID NO: 1 (an expression vector comprising the sequence of the SEQ ID NO: 1). The construction of plasmid pMPT-HBs adw2 includes the following steps:

The HBsAg adw2 gene was synthesized according to the DNA sequence of SEQ ID NO: 1; and the glycerol strain containing the HBsAg adw2 gene plasmid was constructed and named as MC407B-16.

The correctly sequenced MC407B-16 plasmid was digested with EcoRI/BamHI, and the digested product was used a TaKaRa PCR Fragment Recovery Kit (Code No. D301) to recover 701 bp DNA fragment called Inset DNA6.

The correct plasmid pMPT-02 was digested with EcoRI/BamHI, and the vector DNA obtained from the DNA recovery kit was called Vector DNA6.

Inset DNA6 was ligated to Vector DNA6 by using Solution of the TaKaRa DNA Ligation Kit (Code No. D6022), and then thermally transformed into *E. coli* Competent Cell JM109 (Code No. D9052), and the cells were plated in the transformation plate and cultured overnight. Single colonies were selected from the transformation plate, and plasmid DNA was extracted. The plasmid DNA was digested with EcoRI/BamHI. The results showed that MC407A+B+C+D-7780 were positive clones.

The plasmid MC407A+B+C+D-77 was sequenced respectively with primer RV-M, M13-47, MC407P1, MC407P2, MC407P3, MC407P4, MC407P5, MC407P6, MC407P7, MC407P8, MC407P9, MC407BF11, MC407BR11 to prove the plasmid pMPT-HBs adw2 were correct.

Second Embodiment

Construction of a recombinant *H. polymorpha* HBsAg engineered strain (i.e., a *H. polymorpha* host cell transformation screening strain includes the sequence of SEQ ID NO: 1).

Figure 5:
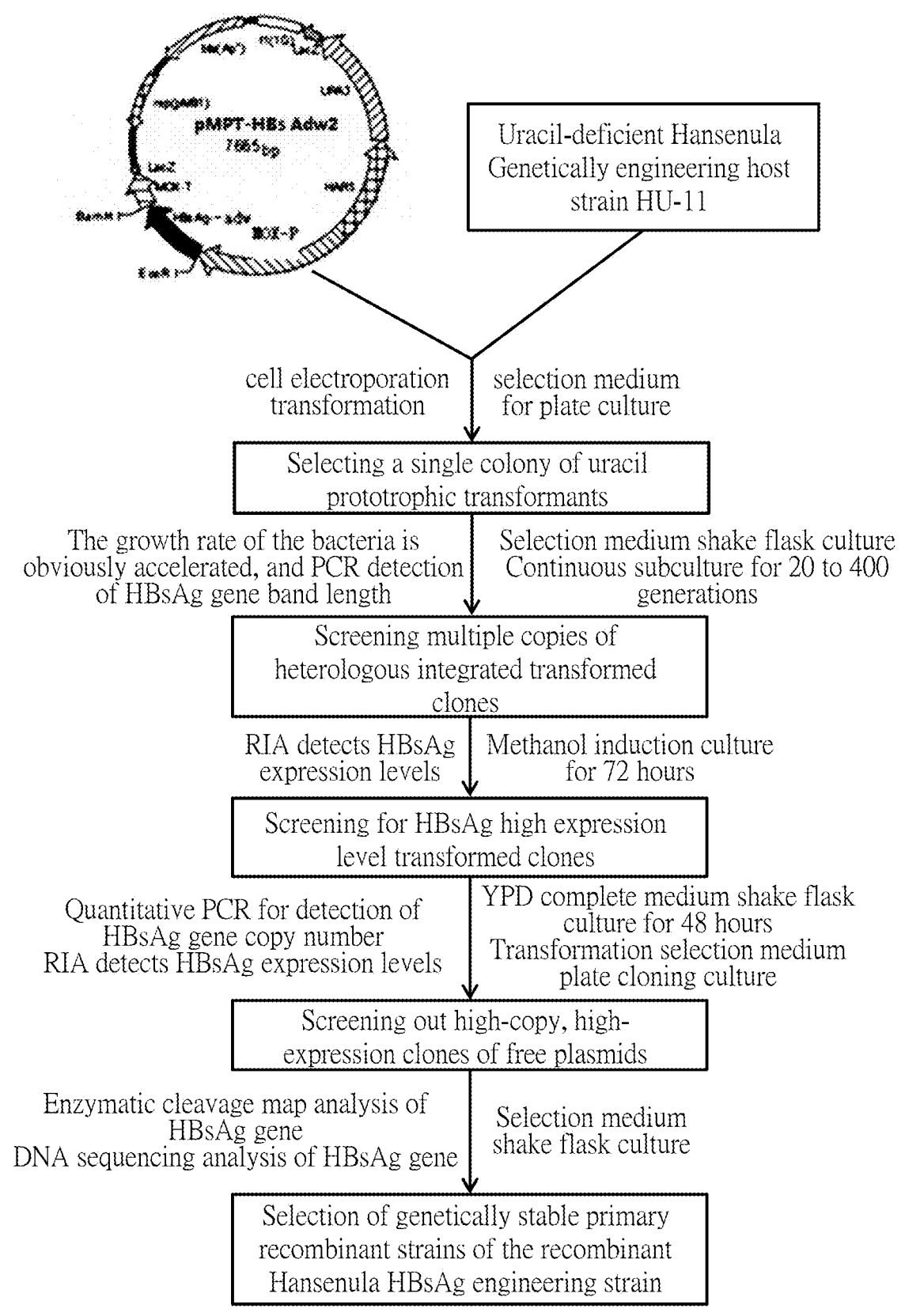

The transformation and screening process of the recombinant *H. polymorpha* was shown in FIG. 5:

Specifically

1) The pMPT-HBsAg plasmid was transformed into the URA3-auxotrophic *H. polymorpha* cell strain HU-11 (CG-MCC No. 1218) of the host cell by cell electroporation. The culture medium was selected using a selection medium (MD liquid medium). The single colony transformants were picked up on the MD selection culture plate and transferred to the MD liquid medium for continuous subculture. The adw2 subtype HBsAg gene and the corresponding regulatory components were multi-copy and heterologously integrated into the host *H. polymorpha* cell chromosome.

2) Strain screening included the following steps (1) Selecting a single colony of uracil prototrophic transformants Colonies with rapid growth rate of bacteria were selected. PCR was used to detect the brightness of HBsAg gene bands. Colonies with a large number of copies were selected, and single colonies were shake-cultured in a selective medium, and successively subcultured for 20 to 400 generations;

(2) Screening multiple copies of heterologous integrated transformed clones

After subculture in step (1), and 72 hours of methanol-induced culture, the expression level of HBsAg released by the disruption of transformant cells was determined by radio immunoassay or radioimmunoassay (RIA);

(3) Screening out high-copy, high-expression clones of free plasmids

The clones screened by step (2) were cultured in YPD complete medium for 48 hours, and then transferred into a selection medium plate for cloning culture, and the HBsAg gene copy number was detected by quantitative PCR, and the expression level of HBsAg was detected by RIA.

(4) Based on the detection result of the step (3), the primary strain of the genetically stabilized recombinant *H. polymorpha* HBsAg engineering strain was selected.

Third Embodiment

The main process of 30 liters of pilot fermentation:

1) strain stored in liquid nitrogen was thawed by 200 ml seed medium, inoculated into the medium, divided into two 0.5 L shake flasks, and cultured at 31° C. for 22 hours as a first-class seed;

2) the primary seed was transferred into the secondary seed culture medium with 1600 ml seed medium, divided into six 1 L shake flasks, and incubate at 31° C. for 20 hours as a secondary seed;

3) 12 L fermentation medium was adjusted to pH 5.5 and transferred into a 30 L fermenter, and then the secondary seed was inoculated under growing at 30-31° C. through two sources of glycerol and methanol; growth, de-repression and induction for the three phases, and co-culture 85 to 96 hours, the cells were harvested after 2-3 hours stopped induction. The frozen cells are homogenized.

Operation Points:

(1) The feeding operation of the growth phase was going when the dissolved oxygen was consumed and the basal medium was consumed; the flow acceleration was gradually increased as the consumption of the basic medium increases, and the flow was added before 2-3 hours the dissolved oxygen was recovered.

(2) In the later stage of the growth phase, pay attention to the dissolved oxygen recovery, record the lowest value of dissolved oxygen, and start to flow when the dissolved oxygen rises to 70-80%, and enter the de-repression phase.

(3) After the later stage of the de-repression phase, the dissolved oxygen began to rise after the end of the flow. When the dissolved oxygen was raised to 70-80% c/o, the methanol induction solution was added, and the methanol concentration is controlled at 3-5; the flow acceleration was controlled by the methanol detection flow controller.

(4) Stopping methanol addition before 2-3 hours the end of fermentation to reduce methanol residue during cell harvest.

Medium

1. Preparation of calcium chloride solution 11.33 g $CaCl_2$ was accurately weighed and put it into a cleaned triangular flask, deionized water was appropriately added to dissolve and dilute to 200 ml.

2. Preparation of micro element solution

Accurately weighting the following reagents:

| | |
|---|---|
| $(NH_4)_2Fe(SO_4)_2 \cdot 6H_2O$ | 1000 mg |
| $CuSO_4 \cdot 5H_2O$ | 80 mg |
| $ZnSO_4 \cdot 7H_2O$ | 300 mg |
| $MnSO_4 \cdot H_2O$ | 400 mg |
| EDTA | 1000 mg |

The weighed reagent was placed in a cleaned triangular flask, dissolved in deionized water and dissolved to 200 ml.

3. Preparation of vitamin solution

Accurately weighting the following reagents:

| | |
|---|---|
| d-Biotin | 6 mg |
| Thiamin HCl | 2000 mg |

Biotin was first dissolved in 10 ml of 50% isopropanol, and then dissolved in Thiamin HCl, and then dissolved in an appropriate amount of deionized water to a volume of 100 ml.

4. Preparation of trace element solution

Accurately weighting the following reagents:

| | |
|---|---|
| $NiSO_4 \cdot 6H_2O$ | 10 mg |
| $CoCl_2 \cdot 6H_2O$ | 10 mg |
| $H_3BO_3$ | 10 mg |
| $Na_2MoO_4 \cdot 2H_2O$ | 10 mg |
| KI | 10 mg |

The weighed reagent was placed in a cleaned triangular flask, and an appropriate amount of deionized solution was added to a volume of 50 ml.

The above four solutions were separately sterilized and filtered for use.

5. Preparation of seed salt solution

Accurately weighting the following reagents:

| | |
|---|---|
| $NH_4H_2PO_4$ | 80 g |
| $MgSO_4 \cdot 7H_2O$ | 18 g |
| KCl | 20 g |
| NaCl | 2 g |

The weighed reagent was placed in a cleaned triangular flask, dissolved in deionized water and dissolved to a volume of 1600 ml.

6. 27 g of glycerin was weighted in a 2000 ml flask, mixed with a salt solution of 360 mL, and made up to 1800 ml with deionized water. The same amount was dispensed into two 2000 ml flasks, and autoclaved at 110° C. for 30 minutes.

Two empty 500 ml triangle bottles, six 1000 ml triangle bottles, a 100 ml graduated cylinder and a 500 ml graduated cylinder all were sterilized under 110° C., 30 minutes high pressure steam.

7. Primary seed medium

In the clean bench, 100 ml of each sterilized glycerin solution was taken aseptically, and added separately into two 500 ml sterilized flasks, and respectively added the following:

| | |
|---|---|
| Calcium chloride solution | 1 ml |
| Micro element solution | 1 ml |
| Vitamin solution | 0.5 ml |
| Trace element solution | 0.25 ml |

Shaking the above solution.

8. Secondary seed medium 1600 ml of sterilized glycerin solution was placed in a clean bench with sterile operation technique and placed in a 2000 ml sterilized triangle, and separately added:

| | |
|---|---|
| Calcium chloride solution | 16 ml |
| Micro element solution | 16 ml |

-continued

| | |
|---|---|
| Vitamin solution | 8 ml |
| Trace element solution | 4 ml |

9. Fermentation medium

The following reagents were accurately weighted and dissolved in 2000 ml of deionized water.

| | |
|---|---|
| $NH_4H_2PO_4$ | 175 g |
| $MgSO_4 \cdot 7H_2O$ | 40 g |
| KCl | 44 g |
| NaCl | 4.4 g |

520 g glycerin was weighted and added into a small 500 ml beaker. 10 ml defoamer was added into the beaker to sterilize, and then added:

| | |
|---|---|
| Calcium chloride solution | 175 ml |
| Micro element solution | 175 ml |
| Vitamin solution | 88 ml |
| Trace element solution | 44 ml |

10. Feed medium 87 g $NH_4H_2PO_4$, 260 g glycerin and 500 ml deionized water were added into 1000 ml flask, and then wrapped feed line and sterilized at 110° C. for 30 minutes.

11. De-repression solution 1800 g glycerin and 660 ml deionized water were added into a 5000 ml flask, and then wrapped feed line and sterilized at 110° C. for 30 minutes. 540 ml filter-sterilized salt solution was added after cooling.

12. Induction solution 400 ml glycerin was added into a 1000 ml flask, and then wrapped feed line and sterilized at 110° C. for 30 minutes. 1600 ml methanol was added aseptically after cooling.

Fourth Embodiment

Purification

The fermentation broth obtained from the third embodiment was harvested and the cells were washed. The detailed steps of purification can be found in References: Li Jin, Kong Yan. Recombinant Hepatitis B Vaccine Production Process. See Li Jin, Yu Yu, Dong Dexiang Editor: Biopharmaceutical Equipment And separation and purification techniques. 1st edition. Beijing: Chemical Industry Press, 2003: 348-349. The harvested cells can be crushed by a homogenizer to release HBsAg; the cell debris was removed by filtration with a 0.22 µm microporous filter; the small molecular impurities were removed by ultrafiltration with a 300K ultramicrofilter; and the HBsAg was extracted by silica gel adsorption treatment. Finally, it was purified by butyl agarose hydrophobic chromatography.

Fifth Embodiment

The Optimal Operating Condition Tests of the Inactivated Recombinant *H. polymorpha* Cell.

In order to determine the optimal conditions for the inactivated recombinant *H. polymorpha*, the following requirements should be met: (1) Reduce the survival rate of the inactivated recombinant *H. polymorpha* less than 5%. (2) Maintain a complete cellular structure to exert as an adjuvant with multi titer activity of the inactivated recombinant *H. polymorpha*. (3) Maintain the HBsAg virus-like particle (VLP) expressed in the inactivated recombinant *H. polymorpha* intact, so as to avoid the antigenicity decline. The above three requirements are the main condition of the production for the inactivated recombinant *H. polymorpha* expressing HBsAg, and would provide the basis for the development of vaccine manufacturing and verification procedures. In addition, the thermal stability of HBsAg virus-like particle (VLP) expressed in the inactivated recombinant *H. polymorpha* is the first issue to be solved.

(1) Preparation of the inactivated recombinant *H. polymorpha* cell with optimal operating condition After the *H. polymorpha* engineering strain (strain number HS604-5) was cultured by fermentation or shake flask induction, the cells were washed with phosphate buffered saline (PBS) for three times by centrifugal process, and suspended the *H. polymorpha* in PBS for the volume calculation. The cells were counted using $OD_{600\ nm}$, diluted to 10 $OD_{600}$ nm/ml with PBS, 2 ml per tube; each test group was provided with two test tubes which were disrupted group and not disrupted group, respectively; 16 test groups were required to prepare 32 tube sample tubes.

Place them in a set temperature water bath and thermally inactivate the recombinant *H. polymorpha* for a set time.

The inactivated recombinant *H. polymorpha* should be cultured for 3 days at 37° C. in a chloramphenicol complete medium agar dish, and the survival rate was counted. The inactivated *H. polymorpha* is stored at 4° C. for further use.

(2) *H. polymorpha* recombinant HBsAg (H5604-5 strain) cell inactivation test group was established:

20° C. room temperature group 1 tube (control)

| | | | |
|---|---|---|---|
| 54° C. | 1 hour | 2 hours | 3 hours |
| 56° C. | 1 hour | 2 hours | 3 hours |
| 58° C. | 1 hour | 2 hours | 3 hours |
| 60° C. | 1 hour | 2 hours | 3 hours |
| 62° C. | 1 hour | 2 hours | 3 hours |

Total is 16 test groups. After inactivation, the HBsAg antigen activity was detected by radioimmunoassay HBsAg reagent; 1:100 dilution and 1:1000 dilution, and double tubes were set. The test results were used to analyze and determine the optimal process conditions for the inactivation of *H. polymorpha* in this new hepatitis B vaccine.

REFERENCES

1. Qi Xiaoqiu, etc., the national population of hepatitis B virus epidemiology investigation report, the first edition of April 2011, People's Health Publishing House.
2. Bowen D G et. al, Intrahepatic immunity: a tale of two sites? Bowen D G et. al, Trends Immunol. 2005, 26(10): 512-7.
3. Thomas H. Kingl, et. al, A Whole Recombinant Yeast-Based Therapeutic Vaccine Elicits HBV X, S and Core Specific T Cells in Mice and Activates Human T Cells Recognizing Epitopes Linked to Viral Clearance, 2014, POLS.
4. Haibin Huang et. al, Robust Stimulation of Humoral and Cellular Immune Responses following Vaccination with Antigen-Loaded (3-Glucan Particles, 2010, MBio. asm. org, 1(3): 1-7.
5. Robert Thimme et. al, CD8+ T Cells Mediate Viral Clearance and Disease Pathogenesis during Acute Hepatitis B Virus Infection, JOURNAL OF VIROLOGY, 2003, p. 68-76.

6. Stefan F. Wieland et. al, Expansion and contraction of the hepatitis B virus transcriptional template in infected chimpanzees. Proc Natl Acad Sci USA. 2004 Feb. 17; 101(7): 2129-2134.
7. John M. Murray et. al, Dynamics of hepatitis B virus clearance in chimpanzees, 2005 Dec. 6; Proc Natl Acad Sci USA. 102(49): 17780-17785.
8. Thimme R et. al, CD8(+) T cells mediate viral clearance and disease pathogenesis during acute hepatitis B virus infection; *J Virol.* 2003 January; 77 (1):68-76.
9. Zeng Zhu-tian, Liver-induced systemic immune tolerance and its reversal, Ph.D thesis, the University of Science and Technology of China, 2014.
10. Applicant: Fudan University, Vaccine for controlling persistent infection of hepatitis B virus, 2009, Publication No. CN102038948A.
11. Florian K Bihl et. al, Simultaneous assessment of cytotoxic T lymphocyte responses against multiple viral infections by combined usage of optimal epitope matrices, anti-CD3 mAb T-cell expansion and "RecycleSpot"; Journal of Translational Medicine 2005, 3: 20 1-19.
12. Yuji Sobao et. al, Identification of hepatitis B virus-specific CTL epitopes presented by HLA-A*2402, the most common HLA class I allele in East Asia, Journal of Hepatology, 2001, 34: 922-929.
13. Applicant: Yuzhang Wu et al., Immunogen for preparation of therapeutic vaccines or drugs for treatment of hepatitis B and the producing method and use thereof, Publication No. CN1483736A.

What is claimed is:

1. A hepatitis B therapeutic vaccine based on inactivated whole recombinant *Hansenula polymorpha* cells expressing HBsAg, wherein the hepatitis B therapeutic vaccine uses the inactivated whole recombinant *Hansenula polymorpha* cells as an adjuvant, the intracellular expression level of HBsAg in the recombinant *Hansenula polymorpha* cells is 6-10 μg HBsAg per $10^8$ cells; and each HBsAg has 19 HBsAg-specific CTL epitopes, and the DNA sequence expressed by the recombinant *Hansenula polymorpha* cell is shown as SEQ ID NO: 1.

2. The hepatitis B therapeutic vaccine according to claim 1, wherein the HBsAg expressed by the recombinant *Hansenula polymorpha* cells comprises SEQ ID NO: 2.

3. The hepatitis B therapeutic vaccine according to claim 1, wherein the HBsAg expressed by the recombinant *Hansenula polymorpha* cells is a virus-like particle structure, which is formed by inserting HBsAgs into *Hansenula polymorpha* lipid, and wherein 9 to 12 among the 14 cysteic acids of the HBsAg form disulfide bonds.

4. The hepatitis B therapeutic vaccine according to claim 1, wherein the host *Hansenula polymorpha* cell line of the recombinant *Hansenula polymorpha* cells is HU-11, and the accession number is CGMCC No. 1218, and the disrupted DNA sequence of the orphanin-5-phosphate decarboxylase gene of the host *Hansenula polymorpha* is shown in SEQ ID NO: 3.

5. The hepatitis B therapeutic vaccine according to claim 1, further comprising HBsAg stock solution or aluminum adjuvant HBsAg.

6. A recombinant *Hansenula polymorpha*, wherein the recombinant *Hansenula polymorpha* comprises the nucleotide sequence of SEQ ID NO: 1, and the nucleotide sequence of SEQ ID NO: 1 is integrated into the genome of the recombinant *Hansenula polymorpha*.

7. The hepatitis B therapeutic vaccine according to claim 2, wherein the dosage form of the hepatitis B therapeutic vaccine is selected from pre-filled injection solution, injection solution, or lyophilized powder injection.

8. The hepatitis B therapeutic vaccine according to claim 1, wherein the dosage form of the hepatitis B therapeutic vaccine is selected from pre-filled injection solution, injection solution, or lyophilized powder injection.

9. The hepatitis B therapeutic vaccine according to claim 2, wherein the dosage form of the hepatitis B therapeutic vaccine is selected from pre-filled injection solution, injection solution, or lyophilized powder injection.

10. The hepatitis B therapeutic vaccine according to claim 3, wherein the dosage form of the hepatitis B therapeutic vaccine is selected from pre-filled injection solution, injection solution, or lyophilized powder injection.

* * * * *

SEQUENCE LISTING

```
<160> NUMBER OF SEQ ID NOS: 3

<210> SEQ ID NO 1
<211> LENGTH: 681
<212> TYPE: DNA
<213> ORGANISM: Artificial sequence
<220> FEATURE:
<223> OTHER INFORMATION: the sequence is synthesized

<400> SEQUENCE: 1
atggagaaca tcacttcagg gtttctagga cctctcctgg tgttgcaggc gggcttcttc      60
ctgttgaccc gaatcctcac cataccgcag agtctggata gctggtggac gtctctcaac     120
tttctcggcg gctcccctgt ctgtctcggc cagaactcgc aatcccctac ctctaaccac     180
tcgccaacct cttgtcctcc aatttgtcca ggttaccgct ggatgtgtct gaggcggttt     240 atcattttc tcttcatctt gctcctgtgc cttatcttct tgttggtgct gcttgactat      300
cagggcatgt tgccagtctg ccctctgatc cctggatcta ctacgacttc tactggtcca     360
tgcaagacgt gcactacccc cgcccaagga aactccatgt tcccctcctg ctgttgcacg     420
aagcctaccg acggcaattg cacctgcatc ccgatcccat cgtcgtgggc attcgctaag     480
tatctgtggg agtgggccag cgtcagattc tcttggctct cccttctagt gccattcgtc     540
caatggttcg taggcctttc cccgactgtt tggcttttccg ccatttggat gatgtggtat    600
tggggtccat cgctctacag cattgttagt cccttatcc cactgctgcc cattttcttt      660
tgcctttggg tttacatcta a                                               681

<210> SEQ ID NO 2
<211> LENGTH: 226
<212> TYPE: PRT
<213> ORGANISM: Artificial sequence
<220> FEATURE:
<223> OTHER INFORMATION: the sequence is synthesized

<400> SEQUENCE: 2

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
```

```
            65                  70                  75                  80
Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
            115                 120                 125

Gln Gly Asn Ser Met Phe Pro Ser Cys Cys Cys Thr Lys Pro Thr Asp
            130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile
            195                 200                 205

Val Ser Pro Phe Ile Pro Leu Leu Pro Ile Phe Phe Cys Leu Trp Val
            210                 215                 220

Tyr Ile
225

<210> SEQ ID NO 3
<211> LENGTH: 797
<212> TYPE: DNA
<213> ORGANISM: Artificial sequence
<220> FEATURE:
<223> OTHER INFORMATION: the sequence is synthesized

<400> SEQUENCE: 3
atgtataaat cttatggaga aagggcgaag tgaagtctca cccatctaag gtcgccagca      60
gactacttaa tttgatggaa tccaagcaaa caaacctctg cgcttctgtg gatgtgacta    120
aaactcagga attattggag cttcttgata aactgggccc ttacatctgc cttgtcaaaa    180
ctcatattga catagtagag gacttctctt atgaacacac cattttacca ttacaggact    240
tgcaaagaaa cacaacttca tgattttga agacagaaag tttgctgata ttaggaaaca    300
cagtcaaact acagtataag ggaggaattt atcgaacatc caagtgggcc gatatcacga    360
atgcacacgg agtgactggc gcaggaattg ttgaaggtct taaacaggcc gcagaagaaa    420
gtacagatga gccacgtggg ctttgatgc ttgctgagct ctcttcaaag ggatcattag    480
ctaccggtga gtatactcaa aaaactgtgg aaatagcgaa aagcgataaa gaatttgtca    540
ttggatttat tgcacagaga gacatggag gtcgtgagga aggctttgac tggctgatca    600
tgactccagg agttggttta gatgataaag gtgattctct gggccaacag tacagaactg    660
ttgatgaagt gatgcaaaca ggaaccgatg tcattatcgt tggaagaggt ttattcggaa    720
aaggaagaga tcctgaagtg aagggaaga gatacagaaa tgctgggtgg gaagcttaca    780
agcggcgcat tgcttaa                                                  797
```